United States Patent
Abuzaina et al.

(10) Patent No.: US 10,806,455 B2
(45) Date of Patent: Oct. 20, 2020

(54) SURGICAL INSTRUMENT FOR DISPENSING TACKS AND SOLUTION

(71) Applicant: Covidien LP, Mansfield, MA (US)

(72) Inventors: Ferass Abuzaina, Highlands Mills, NY (US); Amin Elachchabi, Hamden, CT (US); Ali Irfan, Shelton, CT (US); Gregory Fischvogt, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 536 days.

(21) Appl. No.: 15/582,806

(22) Filed: May 1, 2017

(65) Prior Publication Data

US 2017/0231631 A1   Aug. 17, 2017

Related U.S. Application Data

(62) Division of application No. 13/835,223, filed on Mar. 15, 2013, now Pat. No. 9,655,621.

(51) Int. Cl.
| | | |
|---|---|---|
| *A61B 17/10* | (2006.01) | |
| *A61B 17/064* | (2006.01) | |
| *A61B 17/068* | (2006.01) | |
| *A61B 17/08* | (2006.01) | |
| *A61B 17/00* | (2006.01) | |

(52) U.S. Cl.
CPC ............ *A61B 17/10* (2013.01); *A61B 17/064* (2013.01); *A61B 17/068* (2013.01); *A61B 17/08* (2013.01); *A61B 2017/00367* (2013.01); *A61B 2017/0648* (2013.01)

(58) Field of Classification Search
None
See application file for complete search history.

(56) References Cited

U.S. PATENT DOCUMENTS

| | | | |
|---|---|---|---|
| 3,866,510 A | | 2/1975 | Eibes et al. |
| 4,392,493 A | * | 7/1983 | Niemeijer ............ A61B 17/205 606/116 |
| 4,840,626 A | * | 6/1989 | Linsky .................. A61L 31/042 514/56 |
| 4,884,572 A | | 12/1989 | Bays et al. |
| 5,085,661 A | | 2/1992 | Moss |
| 5,171,247 A | | 12/1992 | Hughett et al. |
| 5,171,249 A | | 12/1992 | Stefanchik et al. |
| 5,176,306 A | | 1/1993 | Helmerl et al. |

(Continued)

FOREIGN PATENT DOCUMENTS

| | | |
|---|---|---|
| DE | 10300787 A1 | 9/2004 |
| DE | 10 2010 015009 A1 | 10/2011 |

(Continued)

OTHER PUBLICATIONS

Chinese First Office Action corresponding to Chinese Patent Appln. No. 201480037169.2 dated Jun. 29, 2017.

(Continued)

*Primary Examiner* — Julie A Szpira

(57) ABSTRACT

A surgical tack applier comprising a handle assembly, an inner tube, a plurality of fasteners and a solution is disclosed. The handle assembly includes an actuator associated therewith. The inner tube extends distally from the handle assembly and defines a longitudinal axis. The inner tube is rotatable about the longitudinal axis. The plurality of fasteners are disposed at least partially within the inner tube and are selectively ejectable therefrom. The solution is disposed within the inner tube and is dispensable through a distal opening of the inner tube.

22 Claims, 13 Drawing Sheets

(56) References Cited

U.S. PATENT DOCUMENTS

| | | | |
|---|---|---|---|
| 5,207,697 A | 5/1993 | Carusillo et al. | |
| 5,228,256 A | 7/1993 | Dreveny | |
| 5,236,563 A | 8/1993 | Loh | |
| 5,246,441 A | 9/1993 | Ross et al. | |
| 5,246,450 A | 9/1993 | Thornton et al. | |
| 5,258,000 A | 11/1993 | Gianturco | |
| 5,312,023 A | 5/1994 | Green et al. | |
| 5,330,487 A | 7/1994 | Thornton et al. | |
| 5,344,061 A | 9/1994 | Crainich | |
| 5,356,064 A | 10/1994 | Green et al. | |
| 5,381,943 A | 1/1995 | Allen et al. | |
| 5,382,254 A | 1/1995 | McGarry et al. | |
| 5,398,861 A | 3/1995 | Green | |
| 5,403,327 A | 4/1995 | Thornton et al. | |
| 5,433,721 A | 7/1995 | Hooven et al. | |
| 5,439,468 A | 8/1995 | Schulze et al. | |
| 5,466,243 A | 11/1995 | Schmieding et al. | |
| 5,467,911 A | 11/1995 | Tsuruta et al. | |
| 5,474,566 A | 12/1995 | Alesi et al. | |
| 5,474,567 A | 12/1995 | Stefanchik et al. | |
| 5,522,844 A | 6/1996 | Johnson | |
| 5,527,319 A | 6/1996 | Green et al. | |
| 5,553,765 A | 9/1996 | Knodel et al. | |
| 5,562,685 A | 10/1996 | Mollenauer et al. | |
| 5,564,615 A | 10/1996 | Bishop et al. | |
| 5,582,615 A | 12/1996 | Foshee et al. | |
| 5,582,616 A * | 12/1996 | Bolduc | A61B 17/064 606/139 |
| 5,584,425 A | 12/1996 | Savage et al. | |
| 5,588,581 A | 12/1996 | Conlon et al. | |
| 5,601,571 A | 2/1997 | Moss | |
| 5,601,573 A | 2/1997 | Fogelberg et al. | |
| 5,626,613 A | 5/1997 | Schmieding | |
| 5,628,752 A | 5/1997 | Asnis et al. | |
| 5,649,931 A | 7/1997 | Bryant et al. | |
| 5,662,662 A | 9/1997 | Bishop et al. | |
| 5,681,330 A | 10/1997 | Hughett et al. | |
| 5,683,401 A | 11/1997 | Schmieding et al. | |
| 5,685,474 A | 11/1997 | Seeber | |
| 5,697,935 A | 12/1997 | Moran et al. | |
| 5,709,692 A | 1/1998 | Mollenauer et al. | |
| 5,730,744 A | 3/1998 | Justin et al. | |
| 5,732,806 A | 3/1998 | Foshee et al. | |
| 5,735,854 A | 4/1998 | Caron et al. | |
| 5,741,268 A | 4/1998 | Schutz | |
| 5,762,255 A | 6/1998 | Chrisman et al. | |
| 5,782,844 A | 7/1998 | Yoon et al. | |
| 5,810,882 A | 9/1998 | Bolduc et al. | |
| 5,824,008 A | 10/1998 | Bolduc et al. | |
| 5,830,221 A | 11/1998 | Stein et al. | |
| 5,833,695 A * | 11/1998 | Yoon | A61B 17/072 606/139 |
| 5,843,087 A | 12/1998 | Jensen et al. | |
| 5,897,564 A | 4/1999 | Schulze et al. | |
| 5,904,693 A | 5/1999 | Dicesare et al. | |
| 5,910,105 A | 6/1999 | Swain et al. | |
| 5,911,722 A | 6/1999 | Adler et al. | |
| 5,928,244 A | 7/1999 | Tovey et al. | |
| 5,928,252 A | 7/1999 | Steadman et al. | |
| 5,931,844 A | 8/1999 | Thompson et al. | |
| 5,941,439 A | 8/1999 | Kammerer et al. | |
| 5,954,259 A | 9/1999 | Viola et al. | |
| 5,961,524 A | 10/1999 | Crombie | |
| 5,964,772 A | 10/1999 | Bolduc et al. | |
| 5,976,160 A | 11/1999 | Crainich | |
| 5,997,552 A | 12/1999 | Person et al. | |
| 6,010,513 A | 1/2000 | Tormala et al. | |
| 6,013,991 A | 1/2000 | Philipp | |
| 6,039,753 A | 3/2000 | Meislin | |
| 6,074,395 A | 6/2000 | Trott et al. | |
| 6,099,537 A * | 8/2000 | Sugai | A61B 17/0684 606/143 |
| 6,126,670 A | 10/2000 | Walker et al. | |
| 6,132,435 A | 10/2000 | Young | |
| 6,146,387 A | 11/2000 | Trott et al. | |
| 6,183,479 B1 | 2/2001 | Tormala et al. | |
| 6,228,098 B1 | 5/2001 | Kayan et al. | |
| 6,235,058 B1 | 5/2001 | Huene | |
| 6,241,736 B1 | 6/2001 | Sater et al. | |
| 6,261,302 B1 | 7/2001 | Voegele et al. | |
| 6,296,656 B1 | 10/2001 | Bolduc et al. | |
| 6,330,964 B1 | 12/2001 | Kayan et al. | |
| 6,387,113 B1 | 5/2002 | Hawkins et al. | |
| 6,402,757 B1 | 6/2002 | Moore, III et al. | |
| 6,425,900 B1 | 7/2002 | Knodel et al. | |
| 6,439,446 B1 | 8/2002 | Perry et al. | |
| 6,440,136 B1 | 8/2002 | Gambale et al. | |
| 6,450,391 B1 | 9/2002 | Kayan et al. | |
| 6,457,625 B1 | 10/2002 | Tormala et al. | |
| 6,491,201 B1 * | 12/2002 | Whitman | A61B 17/1114 227/180.1 |
| 6,551,333 B2 | 4/2003 | Kuhns et al. | |
| 6,562,051 B1 | 5/2003 | Bolduc et al. | |
| 6,572,626 B1 | 6/2003 | Knodel et al. | |
| 6,589,249 B2 | 7/2003 | Sater et al. | |
| 6,592,593 B1 | 7/2003 | Parodi et al. | |
| 6,626,916 B1 | 9/2003 | Yeung et al. | |
| 6,632,228 B2 | 10/2003 | Fortier et al. | |
| 6,652,538 B2 | 11/2003 | Kayan et al. | |
| 6,663,656 B2 | 12/2003 | Schmieding et al. | |
| 6,666,854 B1 | 12/2003 | Lange | |
| 6,695,867 B2 | 2/2004 | Ginn et al. | |
| 6,733,506 B1 | 5/2004 | McDevitt et al. | |
| 6,743,240 B2 | 6/2004 | Smith et al. | |
| 6,749,621 B2 | 6/2004 | Pantages et al. | |
| 6,755,836 B1 | 6/2004 | Lewis | |
| 6,773,438 B1 | 8/2004 | Knodel et al. | |
| 6,800,081 B2 | 10/2004 | Parodi | |
| 6,824,548 B2 | 11/2004 | Smith et al. | |
| 6,837,893 B2 | 1/2005 | Miller | |
| 6,840,943 B2 | 1/2005 | Kennefick et al. | |
| 6,843,794 B2 | 1/2005 | Sixto, Jr. et al. | |
| 6,869,435 B2 | 3/2005 | Blake, III | |
| 6,884,248 B2 | 4/2005 | Bolduc et al. | |
| 6,887,244 B1 | 5/2005 | Walker et al. | |
| 6,893,446 B2 | 5/2005 | Sater et al. | |
| 6,905,057 B2 | 6/2005 | Swayze et al. | |
| 6,929,661 B2 | 8/2005 | Bolduc et al. | |
| 6,942,674 B2 | 9/2005 | Belef et al. | |
| 6,945,979 B2 | 9/2005 | Kortenbach et al. | |
| 6,960,217 B2 | 11/2005 | Bolduc | |
| 6,966,919 B2 | 11/2005 | Sixto, Jr. et al. | |
| 6,988,650 B2 | 1/2006 | Schwemberger et al. | |
| 7,000,819 B2 | 2/2006 | Swayze et al. | |
| 7,128,754 B2 | 10/2006 | Bolduc | |
| 7,143,924 B2 | 12/2006 | Scirica et al. | |
| 7,204,847 B1 | 4/2007 | Gambale | |
| 7,229,452 B2 * | 6/2007 | Kayan | A61B 17/0644 227/179.1 |
| 7,261,716 B2 | 8/2007 | Strobel et al. | |
| 7,491,232 B2 | 2/2009 | Bolduc et al. | |
| 7,670,362 B2 | 3/2010 | Zergiebel | |
| 7,758,612 B2 | 7/2010 | Shipp | |
| 7,862,573 B2 | 1/2011 | Darois et al. | |
| 7,866,525 B2 | 1/2011 | Scirica | |
| 7,867,252 B2 | 1/2011 | Criscuolo et al. | |
| 7,927,327 B2 | 4/2011 | Lu et al. | |
| 7,931,660 B2 | 4/2011 | Aranyi et al. | |
| 8,002,811 B2 | 8/2011 | Corradi et al. | |
| 8,034,076 B2 | 10/2011 | Criscuolo et al. | |
| 8,061,577 B2 | 11/2011 | Racenet et al. | |
| 8,070,033 B2 | 12/2011 | Milliman et al. | |
| 8,075,570 B2 | 12/2011 | Bolduc et al. | |
| 8,087,142 B2 | 1/2012 | Levin et al. | |
| 8,092,492 B2 * | 1/2012 | Hadba | A61B 17/06166 606/151 |
| 8,096,459 B2 | 1/2012 | Ortiz et al. | |
| 8,114,099 B2 | 2/2012 | Shipp | |
| 8,114,101 B2 | 2/2012 | Criscuolo et al. | |
| 8,157,830 B2 * | 4/2012 | Wenchell | A61B 17/00491 606/186 |
| 8,216,272 B2 | 7/2012 | Shipp | |
| 8,221,433 B2 * | 7/2012 | Lozier | A61B 17/068 606/104 |

(56) References Cited

U.S. PATENT DOCUMENTS

| | | | |
|---|---|---|---|
| 8,231,639 B2 | 7/2012 | Bolduc et al. | |
| 8,282,670 B2 | 10/2012 | Shipp | |
| 8,292,933 B2 | 10/2012 | Zergiebel | |
| 8,323,314 B2 | 12/2012 | Blier | |
| 8,328,823 B2 | 12/2012 | Aranyi et al. | |
| 8,343,176 B2 | 1/2013 | Criscuolo et al. | |
| 8,343,184 B2 | 1/2013 | Blier | |
| 8,361,164 B2* | 1/2013 | Hoganson | A61F 2/0063 606/151 |
| 8,382,778 B2 | 2/2013 | Criscuolo et al. | |
| 8,414,627 B2 | 4/2013 | Corradi et al. | |
| 8,465,520 B2 | 6/2013 | Blier | |
| 8,474,679 B2 | 7/2013 | Felix | |
| 8,579,919 B2 | 11/2013 | Bolduc et al. | |
| 8,579,920 B2 | 11/2013 | Nering et al. | |
| 8,597,311 B2 | 12/2013 | Criscuolo et al. | |
| 8,617,184 B2* | 12/2013 | Oepen | A61B 17/0057 227/175.1 |
| 8,668,718 B2* | 3/2014 | Euteneuer | A61B 17/068 606/219 |
| 8,728,120 B2 | 5/2014 | Blier | |
| 8,758,400 B2* | 6/2014 | Ginn | A61B 17/0057 606/213 |
| 8,777,969 B2 | 7/2014 | Kayan | |
| 8,821,522 B2 | 9/2014 | Criscuolo et al. | |
| 8,821,557 B2 | 9/2014 | Corradi et al. | |
| 8,852,215 B2 | 10/2014 | Criscuolo et al. | |
| 8,968,311 B2 | 3/2015 | Allen, IV et al. | |
| 9,186,138 B2 | 11/2015 | Corradi et al. | |
| 9,259,221 B2 | 2/2016 | Zergiebel | |
| 9,655,621 B2 | 5/2017 | Abuzaina et al. | |
| 9,662,106 B2 | 5/2017 | Corradi et al. | |
| 9,668,730 B2 | 6/2017 | Sniffin et al. | |
| 9,801,633 B2 | 10/2017 | Sholev et al. | |
| 9,867,620 B2 | 1/2018 | Fischvogt et al. | |
| 9,987,010 B2 | 6/2018 | Zergiebel | |
| 10,070,860 B2 | 9/2018 | Zergiebel | |
| 2003/0009441 A1 | 1/2003 | Holsten et al. | |
| 2003/0114839 A1 | 6/2003 | Looper et al. | |
| 2004/0043016 A1* | 3/2004 | Redl | A61K 38/363 424/94.64 |
| 2004/0092937 A1 | 5/2004 | Criscuolo et al. | |
| 2004/0111089 A1 | 6/2004 | Stevens et al. | |
| 2004/0127916 A1 | 7/2004 | Bolduc et al. | |
| 2004/0181222 A1 | 9/2004 | Culbert et al. | |
| 2004/0243139 A1 | 12/2004 | Lewis et al. | |
| 2004/0267193 A1* | 12/2004 | Bagaoisan | A61B 17/00491 604/82 |
| 2006/0100629 A1 | 5/2006 | Lee | |
| 2006/0129152 A1 | 6/2006 | Shipp | |
| 2006/0129154 A1 | 6/2006 | Shipp | |
| 2007/0038220 A1 | 2/2007 | Shipp | |
| 2007/0066981 A1* | 3/2007 | Meagher | A61B 17/0644 606/153 |
| 2007/0162030 A1 | 7/2007 | Aranyi et al. | |
| 2007/0175948 A1 | 8/2007 | Scirica et al. | |
| 2008/0083808 A1 | 4/2008 | Scirica | |
| 2008/0086154 A1 | 4/2008 | Taylor et al. | |
| 2008/0097523 A1 | 4/2008 | Bolduc et al. | |
| 2008/0147113 A1 | 6/2008 | Nobis et al. | |
| 2008/0188868 A1 | 8/2008 | Weitzner et al. | |
| 2008/0243106 A1 | 10/2008 | Coe et al. | |
| 2008/0281336 A1 | 11/2008 | Zergiebel | |
| 2008/0281353 A1* | 11/2008 | Aranyi | A61B 17/064 606/219 |
| 2008/0312687 A1 | 12/2008 | Blier | |
| 2009/0118776 A1 | 5/2009 | Kelsch et al. | |
| 2009/0188965 A1 | 7/2009 | Levin et al. | |
| 2010/0030262 A1 | 2/2010 | McLean et al. | |
| 2010/0137999 A1* | 6/2010 | Shohat | A61B 17/00234 623/23.75 |
| 2010/0270354 A1 | 10/2010 | Rimer et al. | |
| 2010/0292710 A1 | 11/2010 | Daniel et al. | |
| 2010/0292713 A1 | 11/2010 | Cohn et al. | |
| 2010/0292715 A1 | 11/2010 | Nering et al. | |
| 2011/0021864 A1* | 1/2011 | Criscione | A61F 2/2481 600/16 |
| 2011/0022065 A1 | 1/2011 | Shipp | |
| 2011/0060349 A1 | 3/2011 | Cheng et al. | |
| 2011/0071578 A1 | 3/2011 | Colesanti et al. | |
| 2011/0079627 A1* | 4/2011 | Cardinale | A61B 17/0642 227/176.1 |
| 2011/0087240 A1 | 4/2011 | Shipp | |
| 2011/0101066 A1 | 5/2011 | Farascioni et al. | |
| 2011/0132964 A1 | 6/2011 | Weisenburgh, II et al. | |
| 2011/0204120 A1 | 8/2011 | Crainich | |
| 2011/0295282 A1 | 12/2011 | Glick et al. | |
| 2012/0059397 A1 | 3/2012 | Criscuolo et al. | |
| 2012/0089131 A1 | 4/2012 | Zemlok et al. | |
| 2012/0109157 A1 | 5/2012 | Criscuolo et al. | |
| 2012/0160892 A1 | 6/2012 | Scirica | |
| 2013/0018392 A1 | 1/2013 | Zergiebel | |
| 2013/0110088 A1 | 5/2013 | Wenchell | |
| 2013/0131700 A1 | 5/2013 | Criscuolo et al. | |
| 2013/0197591 A1 | 8/2013 | Corradi et al. | |
| 2014/0114329 A1 | 4/2014 | Zergiebel | |
| 2014/0121684 A1 | 5/2014 | Criscuolo et al. | |
| 2014/0276967 A1 | 9/2014 | Fischvogt et al. | |
| 2014/0276969 A1 | 9/2014 | Wenchell et al. | |
| 2014/0276976 A1 | 9/2014 | Abuzaina et al. | |
| 2014/0316446 A1 | 10/2014 | Kayan | |
| 2014/0371765 A1 | 12/2014 | Corradi et al. | |
| 2015/0001272 A1 | 1/2015 | Sniffin et al. | |
| 2015/0005748 A1 | 1/2015 | Sniffin et al. | |
| 2015/0005788 A1 | 1/2015 | Sniffin et al. | |
| 2015/0005789 A1 | 1/2015 | Sniffin et al. | |
| 2015/0018847 A1 | 1/2015 | Criscuolo et al. | |
| 2015/0032130 A1 | 1/2015 | Russo | |
| 2015/0080911 A1 | 3/2015 | Reed | |
| 2015/0133970 A1 | 5/2015 | Ranucci et al. | |
| 2015/0133971 A1 | 5/2015 | Ranucci et al. | |
| 2015/0133972 A1 | 5/2015 | Ranucci et al. | |
| 2015/0150558 A1 | 6/2015 | Zergiebel | |
| 2015/0327859 A1 | 11/2015 | Bolduc | |
| 2016/0007991 A1 | 1/2016 | Bolduc | |
| 2016/0007996 A1 | 1/2016 | Bolduc | |
| 2016/0066971 A1 | 3/2016 | Corradi et al. | |
| 2016/0074034 A1 | 3/2016 | Shipp | |
| 2017/0042657 A1 | 2/2017 | Criscuolo et al. | |
| 2017/0128068 A1 | 5/2017 | Zhang et al. | |
| 2017/0151048 A1 | 6/2017 | Russo | |
| 2017/0231631 A1 | 8/2017 | Abuzaina et al. | |
| 2017/0265859 A1 | 9/2017 | Sniffin et al. | |
| 2018/0042591 A1 | 2/2018 | Russo et al. | |
| 2018/0116670 A1 | 5/2018 | Fischvogt et al. | |

FOREIGN PATENT DOCUMENTS

| | | |
|---|---|---|
| EP | 0374088 A1 | 6/1990 |
| EP | 0834280 A1 | 4/1998 |
| EP | 1273272 A2 | 1/2003 |
| EP | 1990013 A1 | 11/2008 |
| EP | 2055241 A2 | 5/2009 |
| EP | 1908409 B1 | 12/2010 |
| EP | 2399538 A2 | 12/2011 |
| EP | 2484294 A1 | 8/2012 |
| EP | 2853202 A2 | 4/2015 |
| JP | 09149906 A | 6/1997 |
| WO | 0016701 A1 | 3/2000 |
| WO | 2002/34140 A2 | 5/2002 |
| WO | 2003034925 A2 | 5/2003 |
| WO | 2003/103507 A2 | 12/2003 |
| WO | 2005004727 A1 | 1/2005 |
| WO | 2004112841 A3 | 7/2005 |
| WO | 2009039506 A1 | 3/2009 |
| WO | 2012064692 A2 | 5/2012 |
| WO | 2013046115 A1 | 4/2013 |

OTHER PUBLICATIONS

Chinese First Office Action corresponding to Chinese Patent Appln. No. 201410418879.1 dated Jun. 29, 2017.

(56) References Cited

OTHER PUBLICATIONS

European Office Action corresponding to European Patent Appln. No. 14 17 8107.0 dated Oct. 12, 2017.
Australian Examination Report No. 1 corresponding to Australian Patent Appln. No. 2014200870 dated Oct. 26, 2017.
Chinese Second Office Action corresponding to Chinese Patent Appln. No. 201410090675 dated Nov. 6, 2017.
Japanese Office Action corresponding to Japanese Patent Appln. No. 2014-048652 dated Nov. 14, 2017.
Japanese Office Action corresponding to Japanese Patent Appln. No. 2014-047708 dated Nov. 14, 2017.
Chinese Second Office Action corresponding to Chinese Patent Appln. No. 2014103063407 dated Feb. 1, 2018.
Australian Examination Report No. 1 corresponding to Australian Patent Appln. No. 2014202970 dated Mar. 9, 2018.
Japanese Office Action corresponding to Japanese Patent Appln. No. 2014-048652 dated Mar. 15, 2018.
Chinese Second Office Action corresponding to Chinese Patent Appln. No. 201480077682.4 dated Mar. 21, 2018.
Australian Examination Report No. 1 corresponding to Australian Patent Appln. No. 2014202972 dated Mar. 27, 2018.
Extended European Search Report corresponding to counterpart Int'l Appln. No. EP 14 81 7036.8 dated Feb. 2, 2017.
European Office Action corresponding to counterpart Int'l Appln. No. EP 14 19 7885.8 dated Feb. 7, 2017.
Chinese First Office Action corresponding to counterpart Int'l Appln. No. CN 201410090675 dated Feb. 28, 2017.
Extended European Search Report corresponding to counterpart Int'l Appln. No. EP 16 19 8333.3 dated Mar. 15, 2017.
European Office Action corresponding to counterpart Int'l Appln. No. EP 14 15 1663.3 dated May 10, 2017.
Extended European Search Report corresponding to counterpart Int'l Appln. No. EP 17 15 7259.7 dated May 10, 2017.
Chinese First Office Action corresponding to counterpart Int'l Appln. No. CN 2014103559671 dated Jun. 13, 2017.
Australian Examination Report No. 1 corresponding to counterpart Int'l Appln. No. AU 2014200071 dated Jun. 20, 2017.
Australian Examination Report No. 1 corresponding to counterpart Int'l Appln. No. AU 2014201338 dated Jul. 10, 2017.
Extended European Search Report corresponding to EP 14 15 9742, completed Jun. 6, 2014 and dated Jun. 20, 2014; (7 pp).
U.S. Appl. No. 61/776,811, filed Mar. 12, 2013, Wenchell et al.
U.S. Appl. No. 61/783,559, filed Mar. 14, 2013, Fischvogt et al.
Extended European Search Report corresponding to EP No. 10 01 2659.8, completed Dec. 21, 2010 and dated Jan. 3, 2011; 3 pages.
Extended European Search Report corresponding to EP No. 10 01 26465, completed Feb. 11, 2011 and dated Feb. 22, 2011; 10 pages.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
Extended European Search Report corresponding to EP 14 15 8946.5, completed Jun. 20, 2014 and dated Jul. 8, 2014; (9 pp).
Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
Extended European Search Report corresponding to counterpart application EP 14 19 7885.8 dated Apr. 30, 2015; 9pp.
Extended European Search Report corresponding to counterpart application EP 14 18 1900.3 dated Apr. 9, 2015; 7pp.
European Office Action corresponding to Patent Application EP 14 15 89465 dated Apr. 26, 2018.
Japanese Office Action corresponding to Patent Application JP 2014-132105 dated May 1, 2018.
Japanese Office Action corresponding to Patent Application JP 2014-047708 dated May 14, 2018.
Chinese Second Office Action corresponding to Patent Application CN 2014103559671 dated May 25, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.

\* cited by examiner

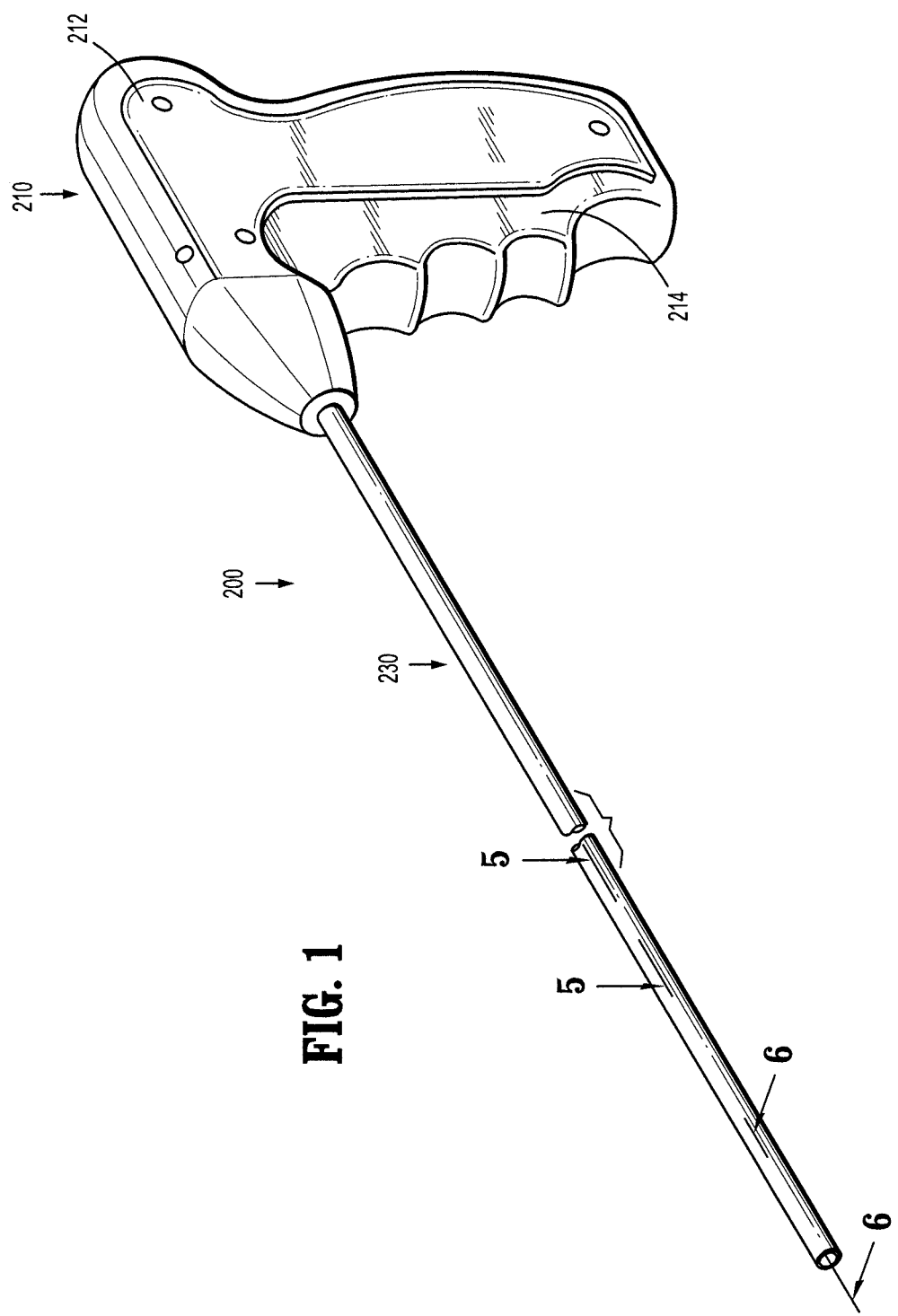

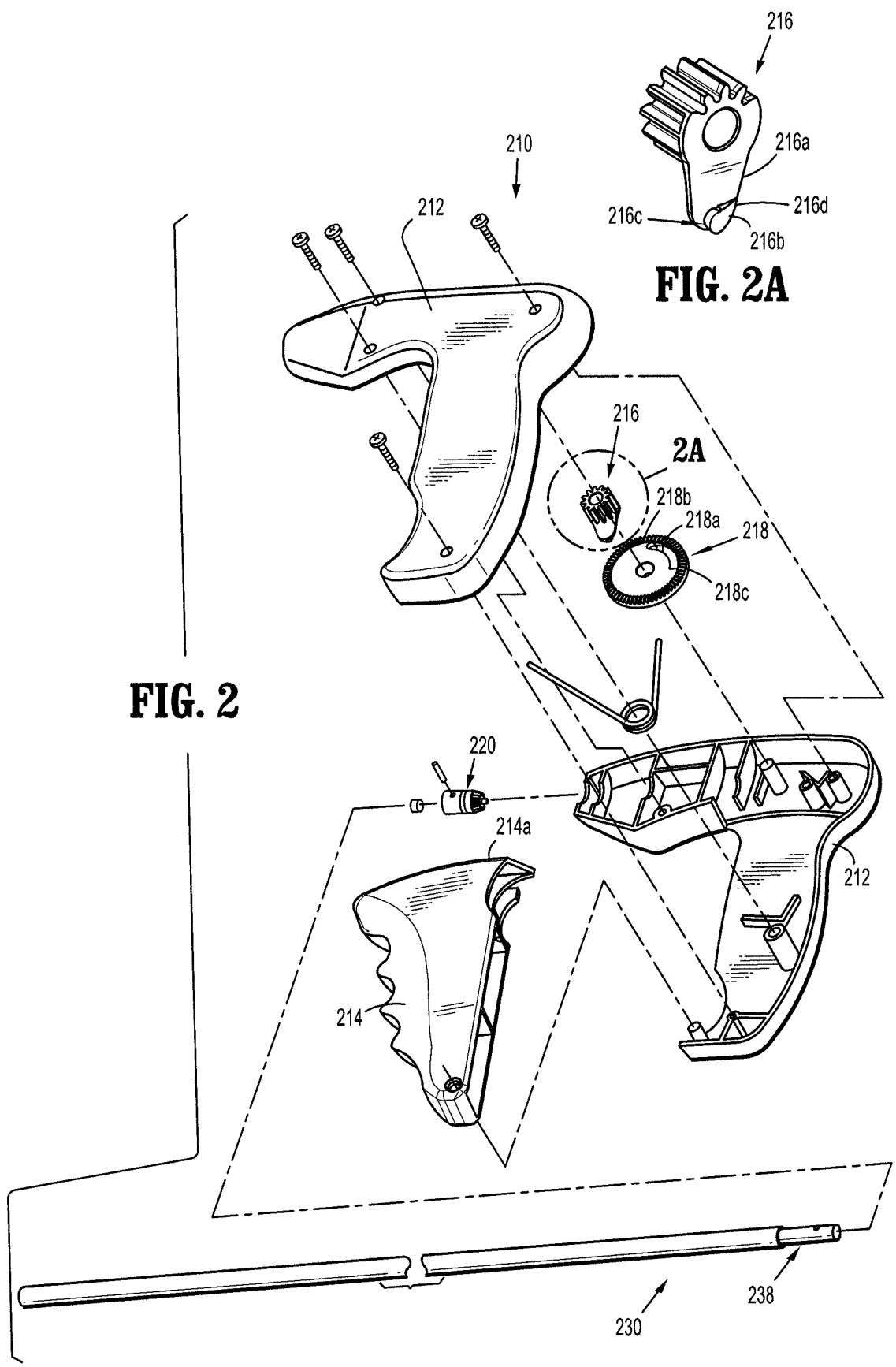

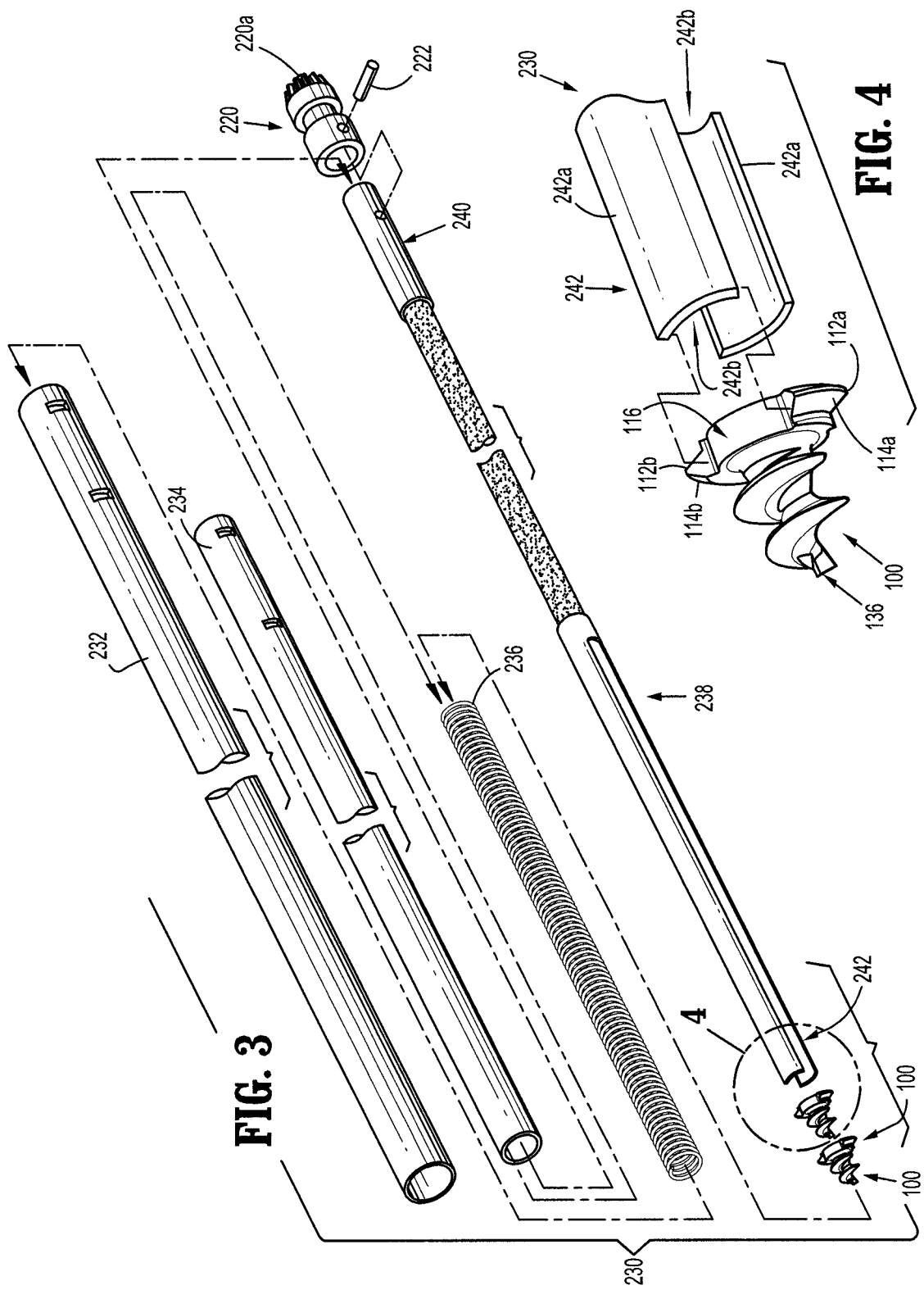

SURGICAL INSTRUMENT FOR DISPENSING TACKS AND SOLUTION

CROSS-REFERENCE TO RELATED APPLICATIONS

This application is a Divisional of U.S. patent application Ser. No. 13/835,223 filed Mar. 15, 2013, the disclosure of the above-identified application is hereby incorporated by reference in its entirety.

BACKGROUND

1. Technical Field

The present disclosure relates to a surgical instrument for dispensing tacks and a solution. More particularly, the present disclosure relates to a tacker instrument for use in applying surgical fasteners through a prosthetic mesh and into tissue and for dispensing a solution adjacent at least some of the tacks.

2. Background of Related Art

Various surgical procedures require instruments capable of applying fasteners to tissue to form tissue connections or to secure objects to tissue. For example, during hernia repair procedures it is often desirable to fasten a mesh to body tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

Less invasive surgical procedures are currently available to repair a hernia. For example, in laparoscopic procedures, the hernia repair surgery is performed through a small incision in the abdomen while in endoscopic procedures, the hernia repair surgery is performed through narrow endoscopic tubes or cannulas inserted through small incisions in the body. Laparoscopic and endoscopic procedures generally require the use of long and narrow surgical instruments capable of reaching deep within the body and configured to seal with the incision or tube they are inserted through. Additionally, the instruments must be capable of being actuated remotely, that is, from outside the body.

Currently, endoscopic techniques for hernia repair utilize fasteners, such as, surgical staples or clips, to secure the mesh to the tissue to provide reinforcement in the repair and structure for encouraging tissue regrowth. The staples or clips are compressed against the tissue and mesh to secure the two together.

One other type of fastener suited for use in affixing mesh to tissue, during procedures such as hernia repair, is a coil fastener having a helically coiled body portion terminating in a tissue penetrating tip or a hollow screw type fastener having an external thread. Unique instruments have been developed to rotate these fasteners into tissue. Examples of some of these types of surgical fasteners and surgical instruments are disclosed in U.S. Pat. Nos. 5,258,000 and 5,830,221, the contents of which are incorporated by reference herein.

In hernia repair surgery, e.g., inguinal or ventral hernia repair, adhesion may occur between the tissue and the fastener. Accordingly, the present disclosure relates to a solution, e.g., a collagen-based paste, that can be applied from the same tube where the fasteners are ejected from, to or adjacent at least some of the ejected fasteners to help minimize adhesion between the fastener and the tissue.

SUMMARY

The present disclosure relates to a surgical tack applier comprising a handle assembly, an inner tube, a plurality of fasteners and a solution. The handle assembly includes an actuator associated therewith. The inner tube extends distally from the handle assembly and defines a longitudinal axis. The inner tube is rotatable about the longitudinal axis. The plurality of fasteners are disposed at least partially within the inner tube and are selectively ejectable therefrom. The solution is disposed within the inner tube and is dispensable through a distal opening of the inner tube.

In disclosed embodiments, the solution is configured to minimize adhesion between a patient's tissue and the plurality of fasteners.

In disclosed embodiments, the solution is selected from the group consisting of a paste, a collagen-based paste, and porcine dermal collagen. Here, it is disclosed that the solution is stored completely within the inner tube. It is further disclosed that the solution is disposed proximally of each of the plurality of fasteners. It is further disclosed that the solution is disposed in contact with each of the plurality of fasteners. It is further disclosed that the entirety of the solution is disposed within the inner tube and proximally of a proximal-most fastener. Here, it is disclosed that the solution is disposed within an ampoule, and wherein the ampoule is disposed completely within the inner tube.

In disclosed that the solution is stored within a plurality of pouches. It is further disclosed that each of the plurality of pouches may be disposed on a portion of an individual anchor.

The present disclosure also relates to a method of applying fasteners to tissue. The method comprises the step of providing a surgical tack applier. The surgical tack applier comprises a handle assembly including an actuator associated therewith, an inner tube extending distally from the handle assembly, defining a longitudinal axis, and being rotatable about the longitudinal axis, a plurality of fasteners disposed at least partially within the inner tube, and a solution disposed within the inner tube. The method also comprises the steps of selectively ejecting at least one of the plurality of fasteners from a distal opening of the inner tube, and dispensing the solution from within the inner tube through the distal opening of the inner tube.

In disclosed embodiments of the method, the solution is selected from the group consisting of a paste, a collagen-based paste and a porcine dermal collagen. Here, it is disclosed that the solution is disposed in a plurality of pouches, and the method further comprises the step of rupturing at least one pouch. It is further disclosed that the entirety of the solution is disposed in an ampoule disposed proximally of a proximal-most anchor, and the method further comprises the step of rupturing the ampoule. It is further disclosed that the step of dispensing the solution from within the inner tube is performed after all of the anchors have been ejected from the inner tube. It is further disclosed that the step of dispensing the solution from within the inner tube is performed while at least one anchor is within the inner tube.

BRIEF DESCRIPTION OF THE DRAWINGS

Embodiments of the present disclosure are described herein with reference to the accompanying drawings, wherein:

FIG. 1 is a perspective view of a surgical tacker instrument in accordance with embodiments of the present disclosure;

FIG. 2 is a perspective, assembly view of the surgical tacker instrument shown in FIG. 1;

FIG. 2a is an enlarged view of the area of detail indicated in FIG. 2;

FIG. 3 is a perspective, assembly view of an anchor retaining/advancing assembly of the surgical tacker instrument of FIG. 1;

FIG. 4 is an enlarged view of the area of detail indicated in FIG. 3;

DETAILED DESCRIPTION OF EMBODIMENTS

Figure 5:
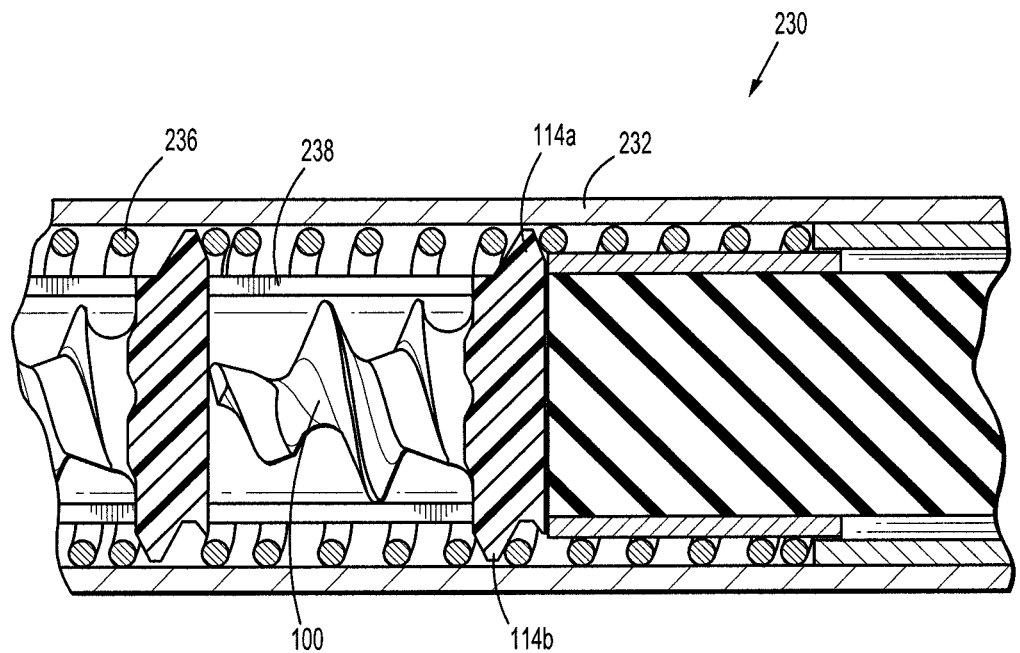
FIG. 5 is a cross-sectional view of a portion of the anchor retaining/advancing assembly taken along line 5-5 in FIG. 1.
Figure 6:
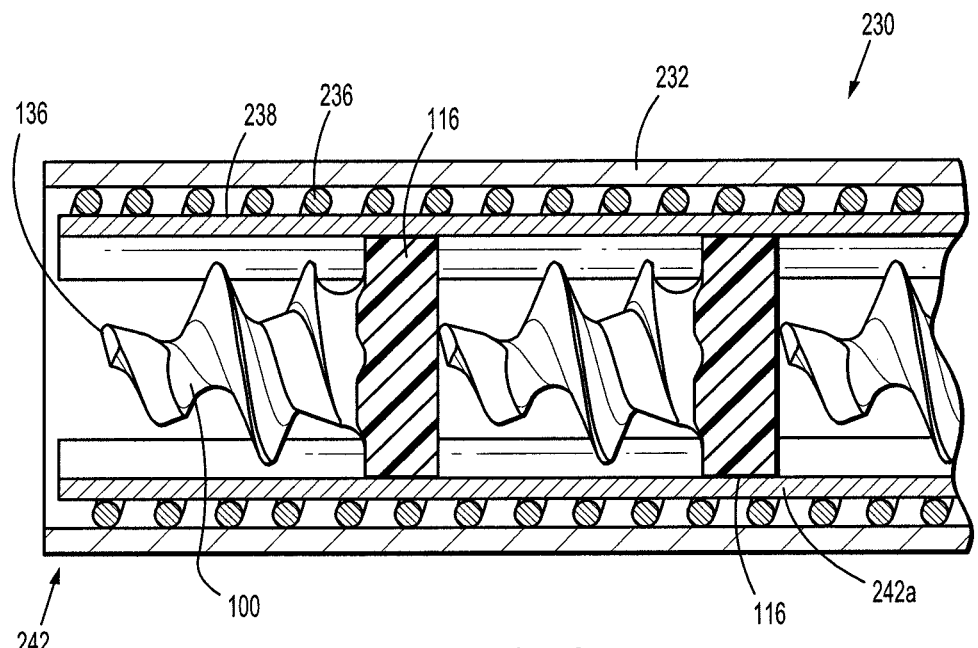
FIG. 6 is a cross-sectional view of a portion of the anchor retaining/advancing assembly taken along line 6-6 in FIG. 1.

Embodiments of the presently disclosed surgical systems, apparatuses and/or devices are described in detail with reference to the drawings, in which like reference numerals designate identical or corresponding elements in each of the several views. As used herein the term "distal" refers to portions of the system, apparatus and/or device, or component thereof, that are farther from the user, while the term "proximal" refers to portions of the system, apparatus and/or device, or component thereof, that are closer to the user.

Referring to FIG. 1, a tacking instrument or tacker 200, for use in installing surgical fasteners in tissue is disclosed. Tacker 200 generally includes a handle assembly 210 and an anchor retaining/advancing assembly 230 extending from handle assembly 210 and configured to store and selectively release or fire a plurality of fasteners or anchors 100 therefrom.

Figure 7:
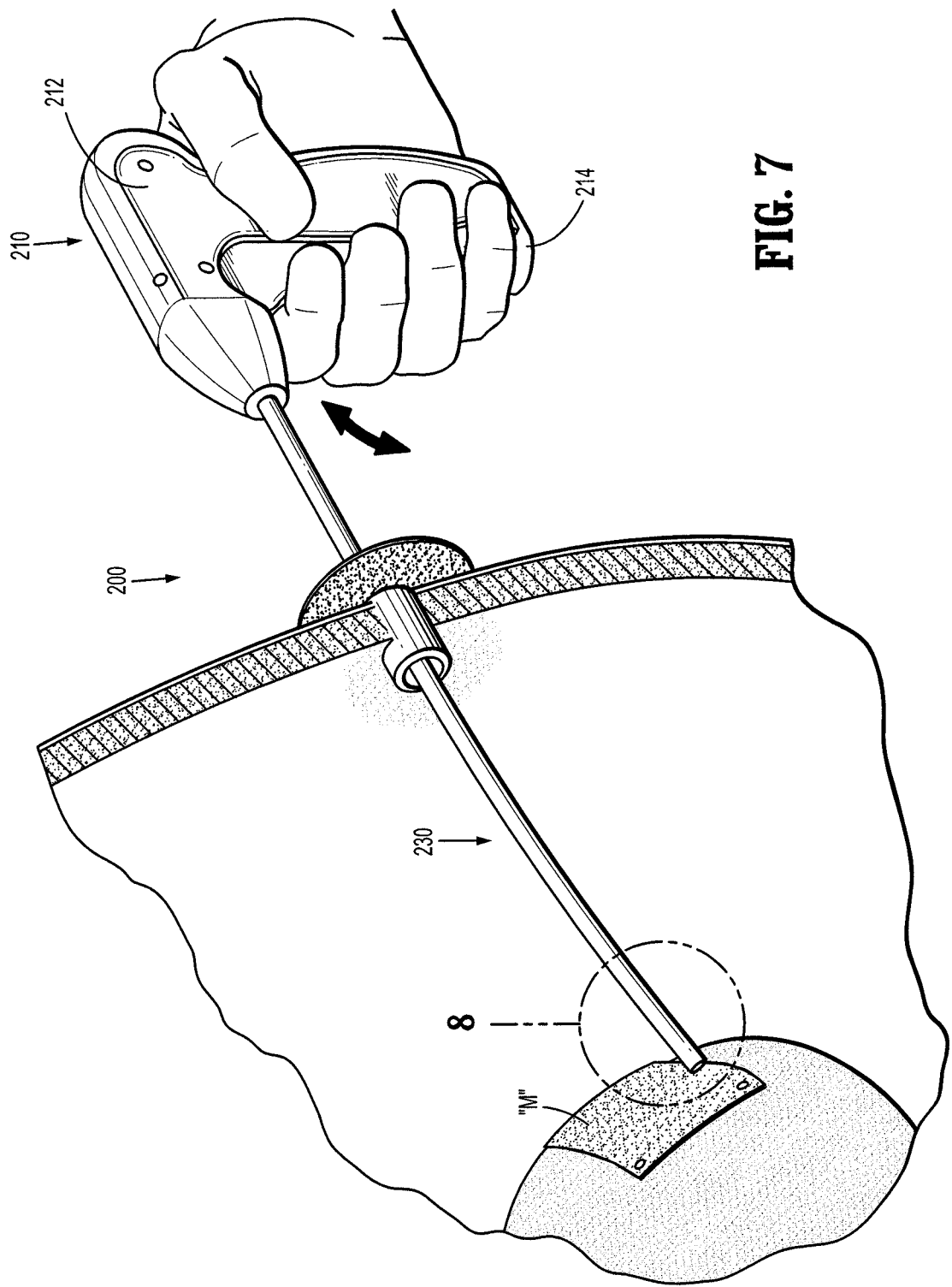
FIG. 7 is an in-situ view of the surgical tacker instrument of the present disclosure applying anchors to mesh and tissue.
Figure 8:
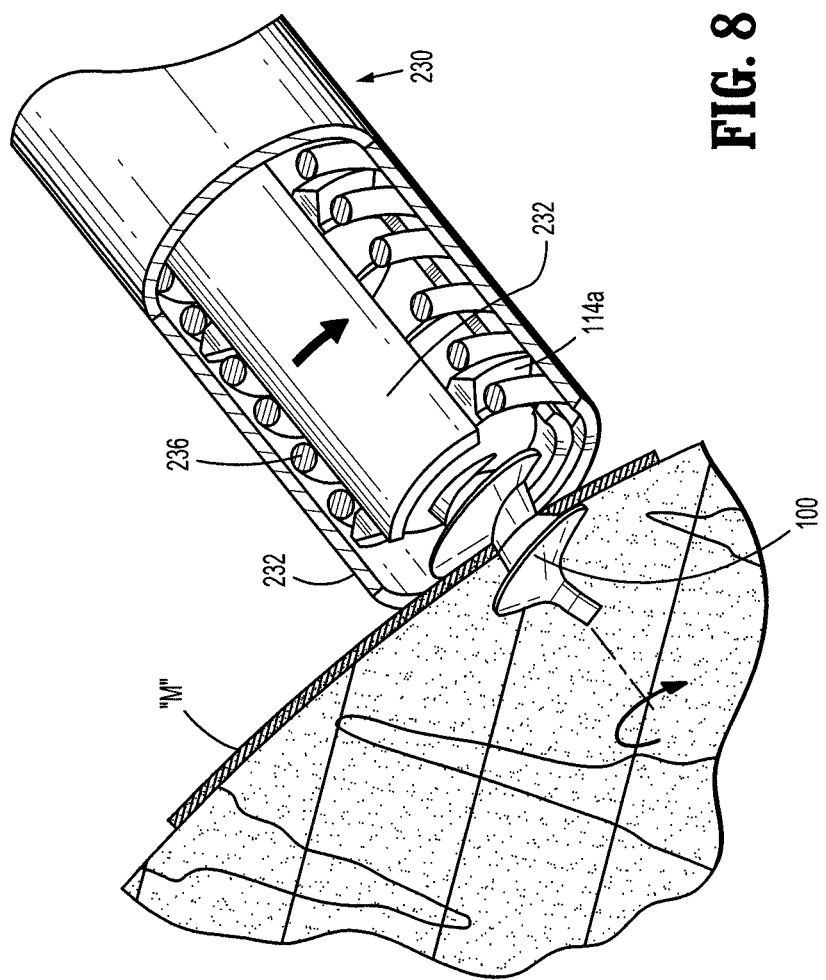
FIG. 8 is an enlarged view of the area of detail indicated in FIG. 7 and further includes a partial cut-away view of a distal portion of the anchor retaining/advancing assembly.

As shown in FIGS. 1, 2 and 7, handle assembly 210 includes a handle housing 212 pivotably supporting a trigger 214. With specific reference to FIG. 2, trigger 214 defines a gear rack 214a formed thereon for operative engagement with a pinion gear 216 rotatably supported in handle housing 212. In disclosed embodiments, gear rack 214a and pinion gear 216 are dimensioned such that one complete squeeze of trigger 214 results in one complete revolution of pinion gear 216. As shown in FIG. 2a, pinion gear 216 includes an arm 216a extending radially therefrom and a cam or ramp 216b extending from arm 216a. Cam 216b includes a front end 216c having a height and tail end 216d tapering into arm 216a.

Handle assembly 210 further includes a bevel gear 218 operatively engaged with pinion gear 216. Bevel gear 218 defines an arcuate slot 218a formed therein for selectively receiving and engaging cam 216b of pinion gear 216. Slot 218a includes a front end wall 218b configured to engage front end 216c of cam 216b of pinion gear 216.

In use, as pinion gear 216 is rotated, upon the squeezing or actuation of trigger 214, front end 216c of cam 216b of pinion gear 216 engages front end wall 218a of slot 218b of bevel gear 218 resulting in concomitant rotation of bevel gear 218. Upon the completion of the actuation of trigger 214 and release thereof, pinion gear 216 rotates in an opposite direction and rear end 216d of cam 216b thereof cams out of slot 218b of bevel gear 218 and along a surface thereof. In disclosed embodiments, pinion gear 216 makes a complete revolution until front end 216c of cam 216b of pinion gear 216 re-engages or clears front end wall 218a of slot 218b of bevel gear 218. As such, cam 216b of pinion gear 216 re-enters slot 218b of bevel gear 218. Bevel gear 218 is maintained from rotating in an opposite direction, upon the opposite direction rotation of pinion gear 216, due to a coefficient of static friction between bevel gear 218 and a surface of handle housing 212 or an axis upon which bevel gear 218 is supported which will tend to maintain bevel gear 218 stationary.

With reference to FIGS. 2 and 3, handle assembly 210 further includes a pinion-bevel gear 220 having gear teeth 220a operatively engaged with gear teeth 218c formed on front end wall 218a of bevel gear 218. Pinion-bevel gear 220 is pinned to a proximal end of an inner tube 238 of anchor retaining/advancing assembly 230.

In use, as described above, upon squeezing of trigger 214, rotation of gear rack 214a causes pinion gear 216 to rotate. Rotation of pinion gear 216 results in rotation of bevel gear 218 and, in turn, rotation of pinion-bevel gear 220 and rotation of anchor retaining/advancing assembly 230.

Referring now to FIGS. 3-6, anchor retaining/advancing assembly 230 includes an outer tube 232 secured to and extending from handle housing 212, a stiffener tube 234 concentrically disposed within outer tube 232, a spiral or coil 236 fixedly disposed within stiffener tube 234 at a location proximate a distal end thereof, and an inner tube 238 rotatably disposed within coil 236.

Inner tube 238 includes a proximal end portion 240 and a distal end portion 242. Proximal end portion 240 of inner tube 238 extends into handle housing 212 and is secured to pinion-bevel gear 220 by a pin 222. Distal end portion 242 of inner tube 238 is slotted, defining a pair of tines 242a and a pair of channels 242b. Distal end portion 242 of inner tube 238 is capable of accepting a plurality of anchors 100 within inner tube 238. In particular, and with additional reference to FIG. 4, anchors 100 are loaded into anchor retaining/advancing assembly 230 such that the pair of opposing threaded sections 112a, 112b of anchors 100 extend through channels 242b of distal end portion 242 of inner tube 238 and are slidably disposed within the groove of coil 236, and the pair of tines 242a of distal end portion 242 of inner tube 238 are disposed within the pair of slotted sections 116 of anchors 100. It is envisioned that each anchor 100 is loaded into anchor retaining/advancing assembly 230 such that adjacent anchors 100 are not in contact with one another so as to not damage distal tips 136 thereof.

In operation, as inner tube 238 is rotated about its longitudinal axis, with respect to coil 236, the pair of tines 242a of inner tube 238 transmits the rotation to anchors 100 and advances anchors 100 distally due to head threads 114a, 114b of anchors 100 engaging with coil 236.

It is envisioned that coil 236 includes twenty-four threads per inch, and the overall length of each anchor 100 is between about 0.1 inches and about 0.3 inches (e.g., approximately equal to 0.203 inches). In such an embodiment, five full turns of inner tube 238 results in anchor 100 being advanced the approximate length of anchor (e.g., 0.203 inches).

Reference may be made to U.S. Provisional Patent Application No. 61/776,811, filed on Mar. 12, 2013, the entire contents of which are incorporated herein by reference, for a further detailed discussion of the construction and operation of tacker 200.

Reference may also be made to U.S. Provisional Patent Application No. 61/783,559, filed on Mar. 14, 2013, the entire contents of which are incorporated herein by reference, for a further detailed discussion of the construction and operation of a tacker which is configured and adapted for articulation and which may incorporate some of the principles of the present disclosure.

Turning now to FIGS. 9-14, a second embodiment of a tacker 1200 is shown. Tacker 1200 is substantially identical to tacker 200 and thus will only be described further herein to the extent necessary to identify differences in construction and/or operation.

As seen in FIGS. 9-14, tacker 1200 is provided with a ratchet mechanism 1260 which is configured to inhibit or prevent inner tube 1238 from backing-out after an anchor 100 has been at least partially driven into tissue. Ratchet mechanism 1260 includes a series of ratchet teeth 1218e formed on a rear end wall 1218d of a bevel gear 1218 (see FIG. 10). Further details of a ratchet mechanism are disclosed in commonly-owned U.S. patent application Ser. No. 10/123,490, the entire contents of which being hereby incorporated by reference herein.

Figure 13:
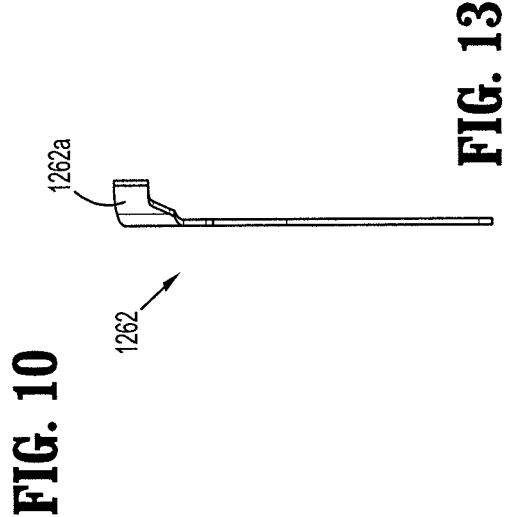
Figure 10:
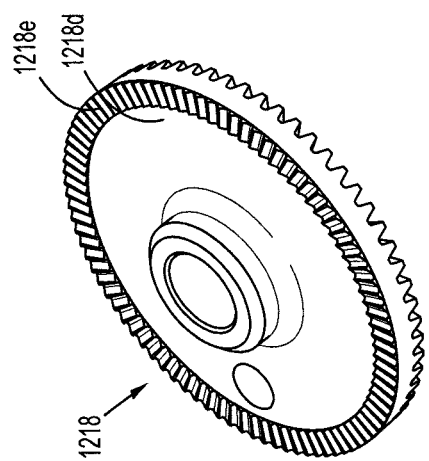
Figure 16:
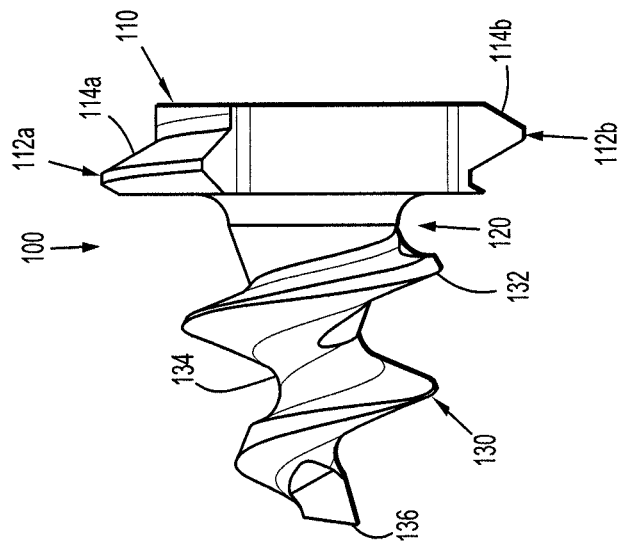
FIGS. 15-18 illustrate various views of an anchor for use in the surgical tacker instrument of FIGS. 1 and 9.
Figure 15:
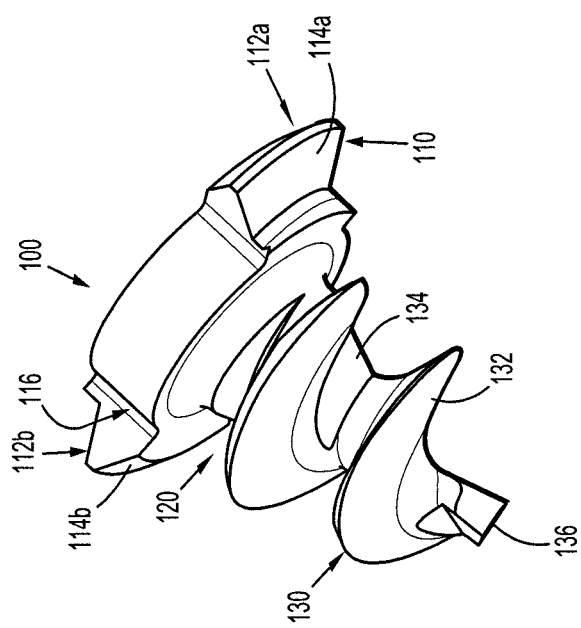

With specific reference to FIG. 13, ratchet mechanism 1260 further includes a spring clip 1262 secured within handle assembly 1210. Spring clip 1262 includes a resilient finger 1262a configured for engagement with ratchet teeth 1218e formed on rear end wall 1218d of bevel gear 1218.

Figure 11:
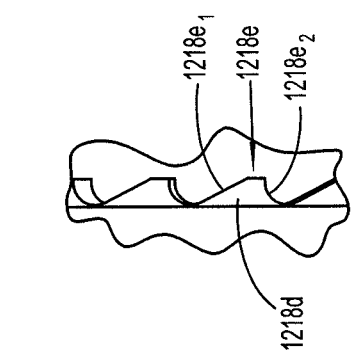

As shown in FIG. 11, each ratchet tooth 1218e includes a shallow angled side 1218$e_1$ and a steep angled side 1218$e_2$. In this manner, resilient finger 1262a of spring clip 1262 engages with ratchet teeth 1218e in such a manner that as bevel gear 1218 is rotated in a first direction resilient finger 1262a cams over shallow angled side 1218$e_1$ of ratchet teeth 1218e. Also, if bevel gear 1218 is rotated in a second direction (opposite to the first direction), resilient finger 1262a stops against steep angled side 1218$e_2$ of ratchet teeth 1218e thereby preventing or inhibiting bevel gear 1218 from rotating in the second direction. As such, any reverse rotation or "backing-out" of anchor 100 or inner tube 1238 (tending to cause bevel gear 1218 to rotate in the second direction), during a driving or firing stroke, is inhibited or prevented.

Figure 9:
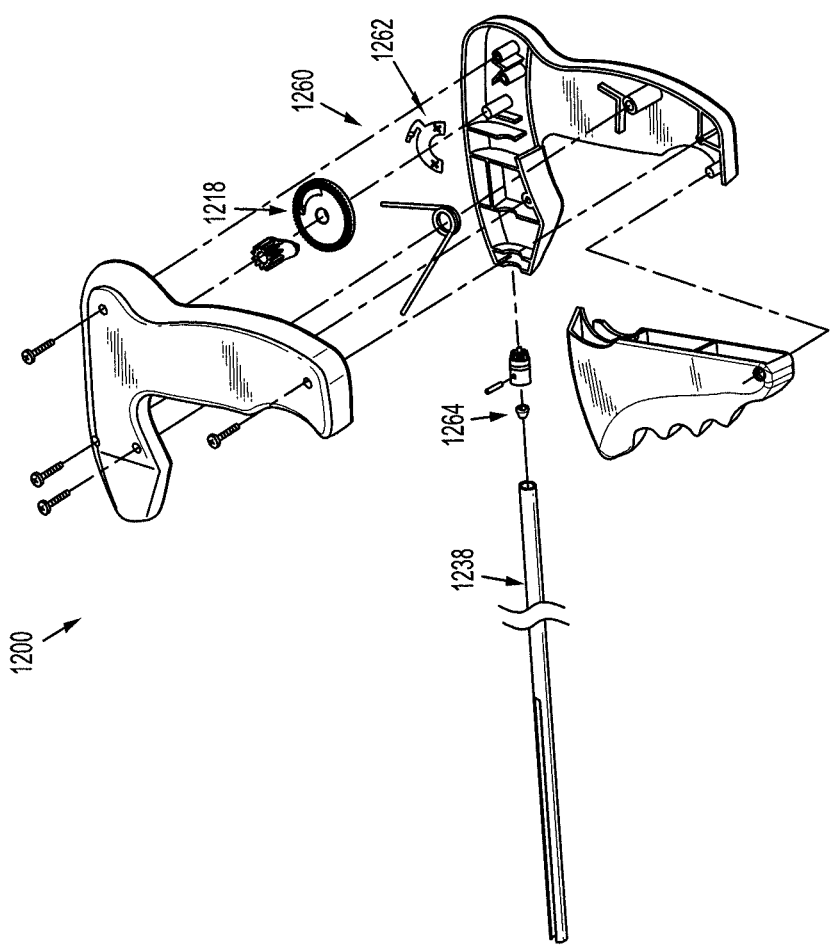
FIG. 9 is a perspective, assembly view of another surgical tacker instrument in accordance with the present disclosure.
Figure 12:
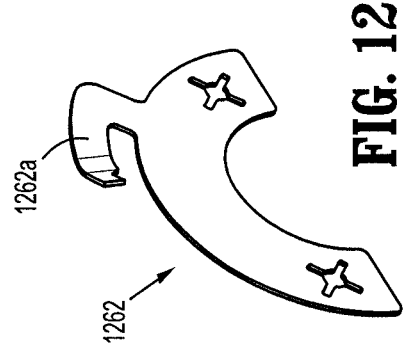
FIGS. 10-14 illustrate various features of the surgical tacker instrument of FIG. 9.
Figure 14:
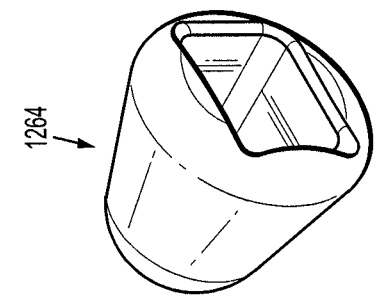

Referring now to FIGS. 9 and 14, tacker 1200 includes a plug 1264 disposed within inner tube 1238. In disclosed embodiments, plug 1264 is fabricated from a polymeric thermoplastic material (Monsanto Santoprene 271-87, available from Monsanto, Inc.) and dimensioned to create a fluid-tight seal within inner tube 1238. In this manner, escape or leakage of insufflations gas (and/or solution 2000, as discussed below) through inner tube 1238 is inhibited or prevented.

With reference to FIGS. 15-18, anchor 100 of the present disclosure, which is usable with tacker 200 and 1200, is shown. Anchor 100 includes a head section 110, a mesh retention section 120, and a threaded tissue-snaring section 130. Head section 110 includes a pair of opposing threaded sections 112a, 112b having respective head threads 114a, 114b, and a pair of opposing open or slotted sections 116a, 116b. A distal surface of head section 110 is formed onto or integral with a proximal end of mesh retention section 120.

Mesh retention section 120 of anchor 100 extends from and between a distal end of head section 110 and a proximal end of tissue-snaring section 130. Mesh retention section 120 functions to lock, anchor or otherwise retain a surgical mesh "M" on to anchor 100 when anchor 100 is screwed into the mesh to a depth past a proximal-most segment 138 of tissue-snaring thread 132. This is achieved because there is no thread located in mesh retention section 120 that would allow the mesh "M" to be unscrewed from anchor 100.

In the illustrated embodiments, mesh retention section 120 is generally cylindrical or conical in shape with a dimension transverse to its longitudinal axis that is smaller than the transverse dimension of head 110 and the transverse dimension of proximal-most segment 138 of tissue-snaring thread 138.

Threaded tissue-snaring section 130 of anchor 100 includes helical threads 132 formed onto a tapered truncated body section 134. A distal point or tip 136 defines the terminus of the distal most tissue-snaring thread 132.

Figure 18:
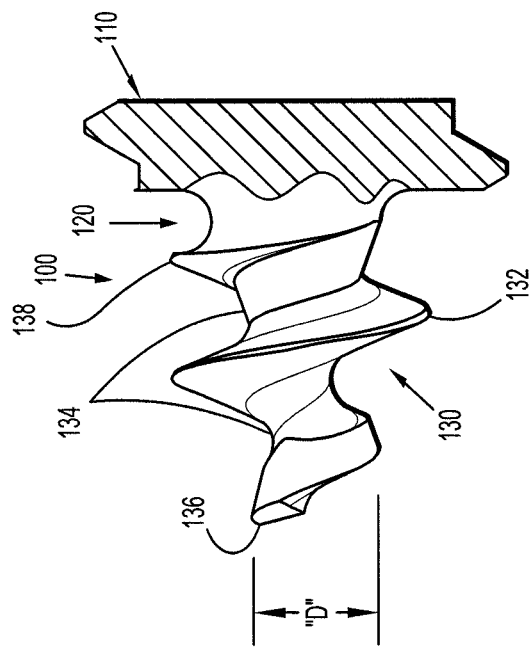
Figure 17:
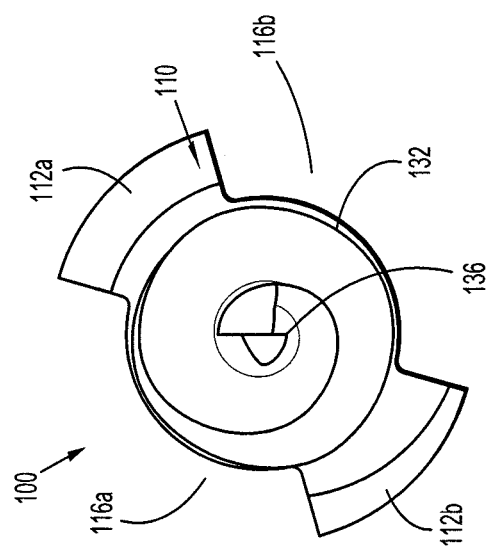

As shown in FIG. 18, body section 134 of tissue-snaring section 130 is tapered, i.e., becoming smaller toward the distal end of threaded tissue-snaring section 130, and terminates, or truncates, distally prior to reaching an apex. Body section 134 includes a concave taper such that, for a given length, a minimum diameter body section 134 is defined upon truncation thereof which is approximately less than 0.01 inches, for example.

Anchor 100 includes a transverse dimension "D" (FIG. 18), of a distal-most thread in the threaded tissue-snaring section 130 which, in disclosed embodiments, is as large as design constraints will allow or approximately greater than 0.040 inches. It is envisioned that a small truncated body diameter and a large value of "D" minimizes tissue indentation. The tissue-snaring threads 132 terminate at distal tip 136, which is distal of the truncation point of body section 134. This geometry allows for ease of mesh penetration and minimizes indentation of the mesh into soft tissue as compared to a non-truncated body with tapered threads.

For a given force applied to a surgical mesh "M" by the surgeon, exerting a distal force on an applier 200, the larger the dimension "D," the less the pressure to cause indentation of an underlying tissue and surgical mesh "M."

Additionally, and with reference to FIGS. 18A-21, tackers 200 and 1200 of the present disclosure are usable with a solution 2000. While solution 2000 is at least usable with tackers 200 and 1200, only its use with tacker 200 is described herein. Solution 2000 may be a paste-like solution, a collagen-based solution, or a collagen paste solution, for example. For instance, solution 2000 may include porcine dermal collagen, which is sold by under the trade name Permacol™. Here, solution 2000 may be an injectable Permacol™ or a Permacol™ paste with a viscosity tailored to the desired application. It is envisioned that Permacol™ sheets or other collagen sheets are cryomilled and prepared into suspensions by mixing the cryomilled power with water and/or saline. Here, the mixing concentration will determine the viscosity of the solution.

Solution 2000 is positioned within inner tube 238 and is dispensible from distal end 242 of inner tube 238, as discussed below. It is envisioned that solution 2000 is formulated to help reduce or prevent adhesion between the surgical mesh "M" and/or anchor 100 and a patient's tissue.

Figure 19:
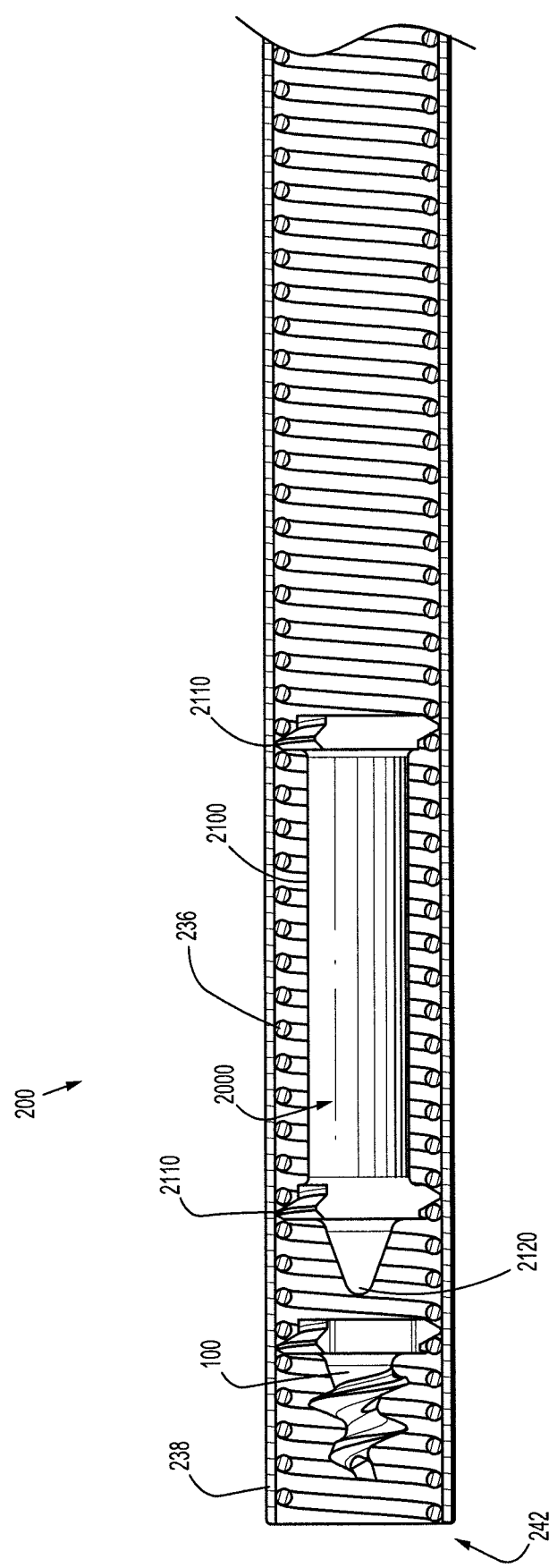
FIGS. 19-21 illustrate various embodiments of the surgical tacker instrument of FIGS. 1 and 9 including a solution therein.

With specific reference to the embodiment illustrated in FIG. 19, the entirety of solution 2000 is disposed within an ampoule 2100. Ampoule 2100 is disposed within inner tube 238 and proximally of the proximal-most anchor 100. It is envisioned that ampoule 2100 includes at least one threaded portion 2110 on at least a portion of its perimeter. In the illustrated embodiment, ampoule 2100 includes two threaded portions 2110: one adjacent its proximal and one adjacent its distal end, but it is envisioned that ampoule 2100 includes more or fewer threaded portions 2110 disposed at any suitable location on or near ampoule 2100. Further, threaded portions 2110 may include any suitable number of threads and may be of any suitable length. As shown, threaded portion 2110 of ampoule 2100 engages coil 236, such that the rotation of bevel gear 220 (and, thus inner tube 238) to cause ejection of anchors 100 also causes ampoule 2100 to advance distally.

In this embodiment, a user initially ejects all anchors 100 from inner tube 238 (e.g., through mesh "M" and into tissue). Continued actuation of tacker 200 advances ampoule 2100 such that solution 2000 therein is able to be dispensed from distal end 242 of inner tube 238 onto/adjacent head section 110 of each anchor 100, for instance. It is envisioned that a distal tip 2120 of ampoule 2100 is frangible. Here, once distal tip 2120 is accessible (e.g., extends distally from inner tube 238), a user may rupture ampoule 2100 by causing distal tip 2120 to contact/depress against anchor 100, mesh "M," or tissue, for example, to cause solution 2000 from within ampoule 2100 to ooze/flow from ampoule 2100. The user can then position distal end 242 of inner tube 238 adjacent each anchor 100, individually, such that solution 2000 oozes/flows onto at least a portion of each anchor 100, for instance.

Figure 20:
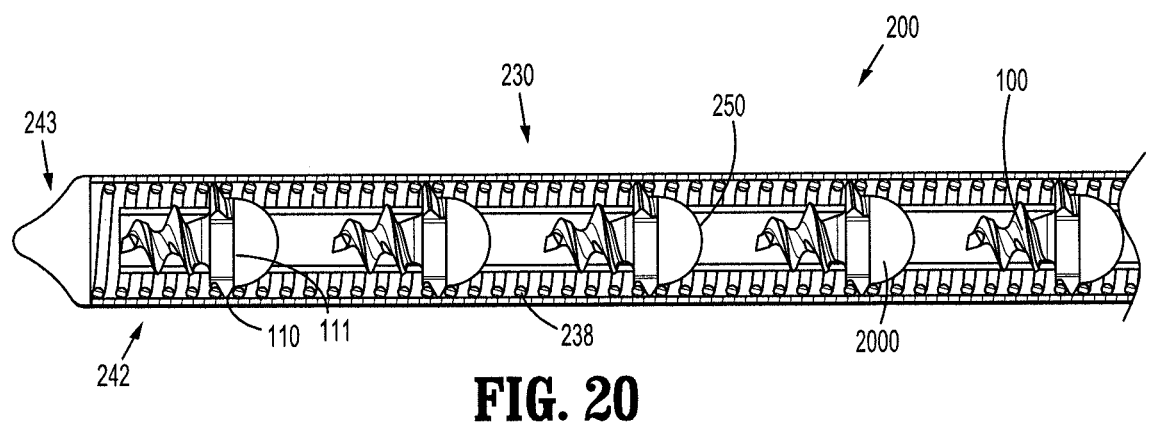

With specific reference to the embodiment illustrated in FIG. 20, solution 2000 is disposed proximally-adjacent, and in contact with, a proximal-facing surface 111 of head section 110 of anchor 100. Here, solution 2000 is mechanically engaged with, adhered to, or otherwise disposed on head section 110 of anchor 100 and is distally advanced along with anchor 100. In this embodiment, solution 2000 is either in direct contact with head section 110, or solution 2000 is enclosed in a puncturable impermeable or semipermeable pouch, sac or membrane 250. It is envisioned that the viscosity of the solution 2000 that is used helps determine whether solution 2000 is in direct contact with head section 110 (solution 2000 has a relatively low viscosity) or whether solution 2000 is enclosed in a pouch 250 (solution 2000 has a relatively high viscosity).

When used in this embodiment, each anchor 100 is ejected from tacker 200 having its own pouch 250 of solution 2000 associated therewith, such that mesh retention section 120, and threaded tissue-snaring section 130 extend at least partially through mesh "M" and into tissue. In the embodiment where solution 2000 is in direct contact with head section 110, it is envisioned that solution 2000 flows/oozes at least partially around head section 110 substantially immediately after firing of anchor 100.

In the embodiment where solution 2000 is enclosed in a pouch 250, pouch 250 (including solution 2000 therein) remains on head section 110 of anchor 100 after anchor 100 is positioned in relation to mesh "M" and the patient. Subsequently, the user of tacker 200 may then use the distal end of anchor retaining/advancing assembly 230 to puncture pouch 250 to cause solution 2000 to be released adjacent anchor 100. Here, it is envisioned that the distal end of anchor retaining/advancing assembly 230 includes a suitable shape (e.g., a point-like) tip 243 (FIG. 20), or knurling, to facilitate puncturing of pouch 250. In this embodiment, it is envisioned that the user punctures each pouch 250 directly after its associated anchor 100 is emplaced through mesh "M" and into tissue. Alternatively, all anchors 100 can be ejected from inner tube 238 prior to pouches 250 being punctured. Any combination of these methods is also envisioned by the present disclosure.

Figure 18A:
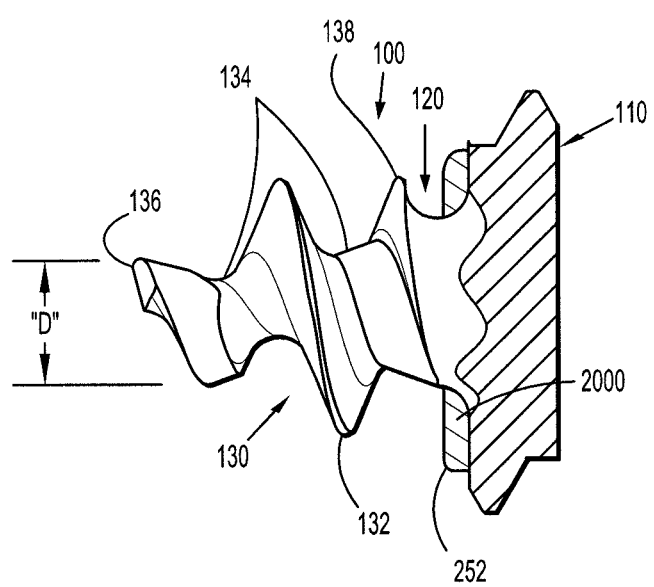
FIG. 18A illustrates an anchor including a solution disposed adjacent a distal surface of a head section.

Additionally, and with reference to FIG. 18A, it is envisioned for solution 2000 to be disposed on the distal surface of head section 110 of anchor 100. In such an embodiment, when solution 2000 is within a pouch 252 disposed on the distal surface of head section 110, it is envisioned that pouch automatically ruptures when anchor 100 is applied through mesh "M." That is, the distal surface of head section 110 compresses pouch 252 against the mesh "M," which results in pouch 252 rupturing, and the solution 2000 flowing/oozing from pouch 252 and around the periphery of head section 110 of anchor 100.

Figure 21:
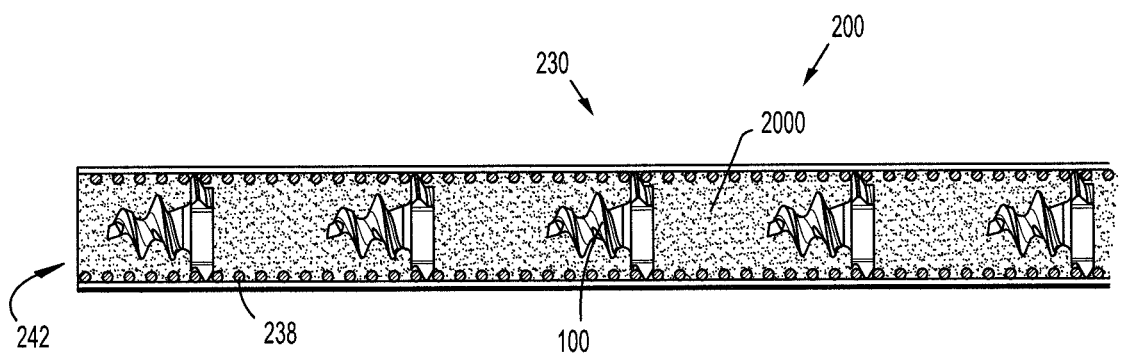

Referring to FIG. 21, another embodiment of tacker 200 is shown. Here, tacker 200 includes a plurality of anchors 100 within inner tuber 238, and also includes solution 2000 filling at least part of the remainder of the volume of inner tube 238. That is, in this embodiment, solution 2000 fills the voids between each anchor 100, proximally of the proximal-most anchor 100, distally of the distal-most anchor 100 and/or between each adjacent anchor 100. Here, when a user actuates handle assembly 120 to eject anchors 100, solution 2000 is automatically dispensed as well. It is envisioned that solution 2000 and anchors 100 are positioned within inner tube 238 during assembly of tacker 200. For example, inner tuber 238 may be injected with a first dosage of solution 2000, loaded with a first anchor 100, injected with a second dosage of solution 2000, followed by a second anchor 100, etc.

Additionally, methods using the disclosed tacker 200, 1200 including solution 2000, are also envisioned and part of the present disclosure.

While the present disclosure relates to anchors 100 and solution 2000 used with a manually-actuatable tacker 200, 1200, it is envisioned that anchors 100 and/or solution 2000 are usable with a powered tacker instrument, such as that described in U.S. Pat. No. 7,931,660 to Aranyi, et al., the entire contents of which being hereby incorporated by reference herein.

It will be understood that various modifications may be made to the embodiments disclosed herein. For example, the disclosed tacker devices may be configured so that the anchor retaining/advancing assembly is removable, and or disposable, from the associated handle assembly. Therefore, the above description should not be construed as limiting, but merely as exemplifications of particular embodiments. Those skilled in the art will envision other modifications within the scope and spirit of the claims appended hereto.

The invention claimed is:

1. A method of applying fasteners to tissue, the method comprising:
   selectively ejecting a first fastener of a plurality of fasteners from a distal opening of an inner tube of a surgical tack applier, wherein the distal opening of the inner tube is the only distal opening of the inner tube;
   storing an entirety of a solution within the inner tube; and
   dispensing the solution from within the inner tube of the surgical tack applier through the distal opening of the inner tube.

2. The method according to claim 1, wherein the solution is selected from the group consisting of a paste and a porcine dermal collagen.

3. The method according to claim 1, wherein the solution is disposed in a plurality of pouches, and wherein the method further comprises rupturing at least one pouch of the plurality of pouches.

4. The method according to claim 1, wherein the solution is contained in an ampoule disposed proximally of a proximal-most fastener of the plurality of fasteners, and wherein the method further comprises rupturing the ampoule.

5. The method according to claim 1, wherein dispensing the solution from within the inner tube is performed after all of the fasteners of the plurality of fasteners have been ejected from the inner tube.

6. The method according to claim 1, wherein dispensing the solution from within the inner tube is performed while at least one fastener of the plurality of fasteners is within the inner tube.

7. The method according to claim 1, wherein the inner tube defines a longitudinal axis extending therethrough, and wherein the method further comprises rotating the inner tube about the longitudinal axis with respect to a handle assembly of the surgical instrument.

8. The method according to claim 1, further comprising engaging each fastener of the plurality of fasteners with a coil disposed within the inner tube.

9. The method according to claim 8, further comprising rotating at least one fastener of the plurality of fasteners with respect to the coil.

10. The method according to claim 1, further comprising contacting each fastener of the plurality of fasteners with the solution.

11. The method according to claim 10, wherein contacting each fastener of the plurality of fasteners with the solution is performed before selectively ejecting at least one fastener of the plurality of fasteners from the distal opening of the inner tube of the surgical tack applier.

12. The method according to claim 1, wherein dispensing the solution from within the inner tube of the surgical tack applier through the distal opening of the inner tube further comprises dispensing the solution such that the solution contacts the at least one fastener that has been ejected from the surgical tack applier.

13. The method according to claim 1, further comprising selectively ejecting a second fastener of the plurality of fasteners from the distal opening of the inner tube of the surgical tack applier, wherein the second fastener is ejected after the first fastener is ejected.

14. The method according to claim 1, wherein the distal opening of the inner tube is aligned with a central longitudinal axis of the inner tube.

15. A method of applying fasteners to tissue, the method comprising:
  selectively ejecting a first fastener of a plurality of fasteners from a distal opening of an inner tube of a surgical tack applier;
  selectively ejecting a second fastener of the plurality of fasteners from the distal opening of the inner tube of the surgical tack applier, wherein the second fastener is ejected after the first fastener is ejected; and
  dispensing a solution from within the inner tube of the surgical tack applier through the distal opening of the inner tube.

16. The method according to claim 15, wherein ejecting the second fastener of the plurality of fasteners from the distal opening of the inner tube of the surgical tack applier occurs before dispensing the solution from within the inner tube of the surgical tack applier through the distal opening of the inner tube.

17. The method according to claim 15, wherein the distal opening of the inner tube is aligned with a central longitudinal axis of the inner tube.

18. The method according to claim 15, wherein the inner tube defines a central longitudinal axis extending therethrough, wherein the distal opening of the inner tube is aligned with the central longitudinal axis, and wherein the method further comprises rotating the inner tube about the central longitudinal axis with respect to a handle assembly of the surgical instrument to move the first fastener away from the handle assembly.

19. A method of applying fasteners to tissue, the method comprising:
  selectively ejecting a first fastener of a plurality of fasteners from a distal opening of an inner tube of a surgical tack applier, wherein the distal opening of the inner tube is the only distal opening of the inner tube;
  dispensing a solution from within the inner tube of the surgical tack applier through the distal opening of the inner tube, wherein the solution is disposed in a plurality of pouches; and
  rupturing at least one pouch of the plurality of pouches.

20. A method of applying fasteners to tissue, the method comprising:
  selectively ejecting a first fastener of a plurality of fasteners from a distal opening of an inner tube of a surgical tack applier, wherein the distal opening of the inner tube is the only distal opening of the inner tube;
  dispensing a solution from within the inner tube of the surgical tack applier through the distal opening of the inner tube, wherein the solution is contained in an ampoule disposed proximally of a proximal-most fastener of the plurality of fasteners; and
  rupturing the ampoule.

21. A method of applying fasteners to tissue, the method comprising:
  selectively ejecting a first fastener of a plurality of fasteners from a distal opening of an inner tube of a surgical tack applier, wherein the distal opening of the inner tube is the only distal opening of the inner tube;
  dispensing a solution from within the inner tube of the surgical tack applier through the distal opening of the inner tube; and
  contacting each fastener of the plurality of fasteners with the solution.

22. A method of applying fasteners to tissue, the method comprising:
  selectively ejecting a first fastener of a plurality of fasteners from a distal opening of an inner tube of a surgical tack applier, wherein the distal opening of the inner tube is the only distal opening of the inner tube;
  dispensing a solution from within the inner tube of the surgical tack applier through the distal opening of the inner tube; and
  selectively ejecting a second fastener of the plurality of fasteners from the distal opening of the inner tube of the surgical tack applier, wherein the second fastener is ejected after the first fastener is ejected.

* * * * *